United States Patent
Arndt et al.

(10) Patent No.: US 7,452,126 B2
(45) Date of Patent: Nov. 18, 2008

(54) MICROMECHANICAL THERMAL-CONDUCTIVITY SENSOR HAVING A POROUS COVER

(75) Inventors: Michael Arndt, Reutlingen (DE); Gerd Lorenz, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 138 days.

(21) Appl. No.: 10/489,008

(22) PCT Filed: Aug. 27, 2002

(86) PCT No.: PCT/DE02/03130

§ 371 (c)(1),
(2), (4) Date: Sep. 20, 2004

(87) PCT Pub. No.: WO03/025557

PCT Pub. Date: Mar. 27, 2003

(65) Prior Publication Data

US 2005/0025215 A1 Feb. 3, 2005

(30) Foreign Application Priority Data

Sep. 12, 2001 (DE) .................................. 101 44 873

(51) Int. Cl.
*G01N 25/18* (2006.01)
*G01N 7/10* (2006.01)
(52) U.S. Cl. ........................... 374/44; 374/29; 374/208; 73/23.25; 73/25.03
(58) Field of Classification Search .................. 374/44, 374/29, 208, 137, 4, 5, 30, 31, 37, 35, 43; 73/23.2, 23.25, 23.4, 25.03, 75; 438/48, 438/54; 436/147; 422/51, 5
See application file for complete search history.

(56) References Cited

U.S. PATENT DOCUMENTS

| | | | | | |
|---|---|---|---|---|---|
| 3,793,605 | A | * | 2/1974 | Fehlner | ........................ 338/34 |
| 4,265,724 | A | * | 5/1981 | Haecker et al. | ............. 204/429 |
| 4,296,148 | A | * | 10/1981 | Friese | ......................... 427/125 |
| 4,334,974 | A | * | 6/1982 | Muller et al. | ................ 204/425 |

(Continued)

FOREIGN PATENT DOCUMENTS

DE        37252        10/1885

(Continued)

OTHER PUBLICATIONS

Patent Abstracts of Japan, vol. 013, No. 482 (P-953), Nov. 2, 1989.

(Continued)

*Primary Examiner*—Gail Verbitsky
(74) *Attorney, Agent, or Firm*—Kenyon & Kenyon LLP

(57) ABSTRACT

A micromechanical thermal-conductivity sensor is provided which includes a thermally insulated diaphragm formed by a recess in a base plate exhibiting poor thermal conductivity. At least one heating element is applied on the diaphragm, at least one temperature-dependent electrical resistor is applied on the diaphragm for measuring the temperature of the diaphragm, as well as at least one further temperature-dependent electrical resistor is applied outside of the diaphragm on the base plate for measuring the ambient temperature. On one or both of its sides, the diaphragm is covered by a porous cover plate permitting gas exchange by diffusion, a cavity being left open between the diaphragm and the porous cover plate.

16 Claims, 3 Drawing Sheets

U.S. PATENT DOCUMENTS

| | | | | |
|---|---|---|---|---|
| 4,400,260 | A * | 8/1983 | Stahl et al. | 204/426 |
| 4,455,378 | A * | 6/1984 | Heiland et al. | 436/126 |
| 4,466,880 | A * | 8/1984 | Torii et al. | 204/428 |
| 4,633,704 | A * | 1/1987 | Tantram et al. | 73/31.05 |
| 4,902,138 | A * | 2/1990 | Goeldner et al. | 374/44 |
| 4,928,513 | A * | 5/1990 | Sugihara et al. | 73/25.03 |
| 4,988,429 | A * | 1/1991 | Matthiessen | 204/408 |
| 5,535,614 | A | 7/1996 | Miyake et al. | |
| 5,557,972 | A * | 9/1996 | Jacobs et al. | 73/756 |
| 5,644,068 | A * | 7/1997 | Okamoto et al. | 73/23.32 |
| 5,811,662 | A * | 9/1998 | Williams et al. | 73/31.06 |
| 5,841,021 | A * | 11/1998 | De Castro et al. | 73/23.2 |
| 5,844,123 | A * | 12/1998 | Marsh et al. | 73/19.12 |
| 5,989,398 | A * | 11/1999 | Young et al. | 204/424 |
| 6,165,336 | A * | 12/2000 | Maki et al. | 204/415 |
| 6,265,222 | B1 * | 7/2001 | DiMeo et al. | 436/144 |
| 6,327,892 | B1 * | 12/2001 | Koiso et al. | 73/38 |
| 6,584,827 | B2 * | 7/2003 | Kiesele et al. | 73/31.05 |
| 6,691,554 | B2 * | 2/2004 | Eastman et al. | 73/25.03 |
| 6,807,843 | B1 * | 10/2004 | Hawe | 73/23.2 |
| 7,022,213 | B1 * | 4/2006 | Austen et al. | 204/432 |
| 7,160,750 | B2 * | 1/2007 | Benzel et al. | 438/48 |
| 7,233,000 | B2 * | 6/2007 | Nassiopoulou et al. | 250/338.4 |
| 7,249,490 | B2 * | 7/2007 | Pendergrass | 73/31.05 |
| 7,282,712 | B2 * | 10/2007 | Shibayama | 250/338.4 |
| 2003/0116813 | A1 * | 6/2003 | Benzel et al. | 257/414 |
| 2003/0177815 | A1 * | 9/2003 | White | 73/31.05 |
| 2004/0265440 | A1 * | 12/2004 | Morris et al. | 426/231 |
| 2005/0042141 | A1 * | 2/2005 | Otani et al. | 422/98 |
| 2005/0205959 | A1 * | 9/2005 | Chau et al. | 257/467 |
| 2006/0117737 | A1 * | 6/2006 | Ohsaki | 60/276 |
| 2007/0007134 | A1 * | 1/2007 | Kawase et al. | 204/406 |

FOREIGN PATENT DOCUMENTS

| | | |
|---|---|---|
| DE | 37 11 511 | 6/1988 |
| DE | 38 37 951 | 5/1990 |
| GB | 2392721 A * | 3/2004 |
| JP | 01 193638 | 8/1989 |
| JP | 09 005278 | 1/1997 |
| WO | WO01/14868 A2 * | 3/2001 |

OTHER PUBLICATIONS

Patent Abstracts of Japan, vol. 1997, No. 05, May 30, 1997.

* cited by examiner

MICROMECHANICAL THERMAL-CONDUCTIVITY SENSOR HAVING A POROUS COVER

FIELD OF THE INVENTION

The present invention relates to a micromechanical thermal-conductivity sensor. In particular, it relates to a micromechanical thermal-conductivity sensor which includes a thermally insulated diaphragm formed by a recess in a base plate exhibiting poor thermal conductivity, at least one heating element applied on the diaphragm, at least one temperature-dependent electrical resistor applied on the diaphragm for measuring the diaphragm temperature ($T_M$), as well as at least one further temperature-dependent electrical resistor, applied outside the diaphragm on the base plate, for measuring the ambient temperature ($T_U$). The present invention also relates to a method for producing the thermal-conductivity sensor, as well as its use.

BACKGROUND INFORMATION

The measurement of thermal conductivity is used frequently for analyzing gases, particularly for the quantitative analysis of two-component gas mixtures.

In principle, it holds true that the thermal conductivity of a gas or gas mixture varies with the mass of the gas molecules, their concentration and the temperature. If the (mixed-) thermal conductivity of the gas or the gas mixture is measured at a known gas temperature and for known components, then it is possible to exactly determine the concentrations of individual components of the gas mixture based on the thermal conductivity. Above all, the concentrations of hydrogen ($H_2$) and helium (He) in the mixture with other gases such as air, oxygen ($O_2$), nitrogen ($N_2$), ammonia ($NH_3$), argon (Ar), carbon dioxide ($CO_2$), carbon monoxide (CO), chlorine ($Cl_2$), hydrogen sulphide ($H_2S$), methane ($CH_4$), nitrogen monoxide (NO), dinitrogen monoxide ($N_2O$) and water vapor ($H_2O$) may be measured well, because these gases have particularly high thermal conductivity compared to the other gases. Thus, the thermal conductivity of hydrogen ($H_2$) is $\lambda_{hydrogen}=0.84$ $Wm^{-1}K^{-1}$ and the thermal conductivity of helium (He) is $\lambda_{helium}=0.6$ $Wm^{-1}K^{-1}$, while the thermal conductivity of air $\lambda_{air}=0.012$ $Wm^{-1}K^{-1}$ is less by approximately a factor 5-7.

To measure the thermal conductivity, a body is brought to a temperature $T_K$ which is higher than the ambient temperature $T_U$. A gas (mixture) surrounding the body is generally at ambient temperature. For example, if the temperature difference $\Delta T=T_K-T_U$ is held constant, then the heating power $P_H$ necessary for this purpose is a measure for the thermal conductivity of the surrounding gas or gas mixture. Heating power $P_H$ is directly proportional to constantly retained temperature difference $\Delta T$; the proportionality constant results from the product of the thermal conductivity $\lambda$ and a (constant) geometry factor K which is a function of the measuring device. This correlation is described in equation (1):

$$P_H = K\lambda\Delta T \tag{1}$$

where $P_H$ designates the heating power, $\Delta T$ designates the temperature difference, K designates the geometry factor and $\lambda$ designates the thermal conductivity.

Recently, micromechanical thermal-conductivity sensors based on silicon are increasingly being developed to determine thermal conductivity. In contrast to conventional thermal-conductivity sensors, these sensors have the feature of low power consumption, which essentially is no greater than the power consumption of the electronic equipment needed for the signal processing. Moreover, the miniaturized sensors possess short response times (time constants) which generally can only be achieved by the acceptance of a forced traversal with the measuring gas, i.e., a flow dependency, in the case of conventional sensors. In the last analysis, however, this makes universal use impossible. Finally, such micromechanical thermal-conductivity sensors based on silicon are economical to produce, because it is possible to fall back on customary methods for the production of integrated semiconductor components.

The design of a typical conventional micromechanical thermal-conductivity sensor based on silicon is shown in FIG. 1 and is described below.

A fundamental problem when measuring the thermal conductivity of a surrounding gas is the heat transfer caused by convection of the gas, accompanied by a falsification of the actual thermal-conductivity value. A convective heat transfer may result from external gas movements which become noticeable in the sensor, but also from the temperature difference, necessary for the measurement, between the heating element and diaphragm, respectively, and the gas.

It may be that a forced traversal of the thermal-conductivity sensor with the gas to be measured is definitely desired in order to permit a rapid gas exchange and therefore short response times; however, for micromechanical thermal-conductivity sensors having very small measuring volumes and an inherently rapid gas exchange thereby permitted, any convective heat transfer is regarded as disadvantageous.

To prevent convective heat transfer, the sensor is usually used in such a way that the gas volume near the diaphragm remains quiet. This may be achieved, for example, by covering the diaphragm with a cover plate.

For example, German Patent No. DE 37 252 describes a micromechanical thermal-conductivity sensor for measuring the thermal conductivity of a gas mixture, in which an insulator layer is applied on a support plate made of silicon, meander-shaped thin-film resistors being applied on the insulator layer by vapor deposition or sputtering. In the region of the thin-film resistors, the insulator layer is undercut so that in the support plate, a hollow is obtained which forms the lower part of the sensor measuring chamber. Resting on the support plate having the thin-film resistors is a silicon cover plate into which a hollow is etched at the height of the thin-film resistors which forms the upper part of the measuring chamber. The cover plate has an opening which, as a diffusion channel, makes it possible for the gas mixture to enter the measuring chamber. The exchange of gas in the lower hollow of the measuring chamber takes place through cutouts in the insulator layer.

The disadvantage in this thermal-conductivity sensor is that the dimensions of the diffusion channel must in any case be selected so that, first of all, the gas in the measuring chamber is exchanged as quickly as possible by diffusion through a large opening, but secondly, gas movements which occur outside of the measuring chamber are not transferred into the measuring chamber, which requires a small opening. However, this objective can only be achieved as a compromise between the two requirements, a given design of the diffusion channel generally no longer permitting a universal application.

SUMMARY

An object of the present invention is to overcome the disadvantages of the conventional micromechanical thermal-conductivity. In particular, a universally applicable thermal-conductivity sensor is provided in which a convective heat transfer through the gas or gas mixture to be measured is avoided to the greatest extent possible.

According to the present invention, a micromechanical thermal-conductivity sensor is described which includes a thermally insulated diaphragm formed by a recess in a base plate exhibiting poor thermal conductivity, at least one heating element (resistance element) applied on the diaphragm, at least one temperature-dependent electrical resistor applied on the diaphragm for measuring the temperature of the diaphragm, as well as at least one further temperature-dependent electrical resistor applied outside of the diaphragm on the base plate for measuring the ambient temperature, and is characterized in that on one or both of its sides, the diaphragm is covered by a porous cover plate permitting gas exchange by diffusion, a cavity being left open between the diaphragm and the porous cover plate. Thus, the thermal-conductivity sensor of the present invention may be provided with one or two porous cover plates, i.e., may have one or two cavities between the diaphragm and cover plate(s).

The porous cover plate(s) advantageously permit diffusion of the surrounding gas or gas mixture into the cavity forming the measuring space, without at the same time the measurement result being falsified by a convection current of the gas. Because of the small dimension of the cavity or cavities, particularly due to its/their low height, the convective heat transfer in the direction of a cover plate caused by the temperature difference between the diaphragm and heating element, respectively, and the cover plate is substantially reduced, so that a convection current of the gas to be measured in a cavity is minimized on the whole and is essentially prevented. The response time of the sensor is sharply reduced by the gas exchange rapidly taking place. Moreover, the sensitivity of the sensor may be increased, because the minimized convection current of the gas or gas mixture to be measured provides the possibility of using a relatively great temperature difference between the diaphragm and the measuring gas. There is also the possibility of using the sensor universally, regardless of the installation situation.

As described above, the porous cover plate may be applied on one or both sides of the (flat) diaphragm. If the porous cover plate is applied on that side of the base plate which has the recess for forming the diaphragm, after the cover plate is applied, this recess forms a cavity which is used as the measuring space for the sensor. If the porous cover plate is applied on the side of the base plate opposite this side, then the porous cover plate must have a recess situated opposite the diaphragm, this recess forming a cavity after the cover plate is applied. This cavity then forms a measuring space for the thermal-conductivity sensor. The sensor may therefore optionally be provided with one or two cavities (i.e., measuring spaces) for the gas (mixture) to be measured.

The base plate is preferably made of silicon. This has the advantage that for the further processing, it is possible to resort to the methods used in semiconductor technology such as vapor deposition methods, sputtering methods, photolithographic methods, etching methods and passivation methods. It is thus possible to produce the sensors in a cost-effective manner. In particular, a plurality of sensors according to the present invention may be produced from a single silicon wafer.

The porous cover plate is preferably made from a porous ceramic material, particularly SiC and $Al_2O_3$. If applicable, the porous cover plate is made at least partially of porous silicon.

Preferably, the thermal expansion coefficient of the ceramic material is essentially equal to the thermal expansion coefficient of silicon, or at least is close to it. In this case, the cover plate(s) and the base plate and diaphragm, respectively, have an equal thermal expansion, which means thermally caused stresses after applying the cover plate on the base plate may advantageously be avoided or minimized.

The thickness of the base plate used for producing the sensor is preferably in the range of 200-600 μm, while the diaphragm preferably has a thickness in the range of 0.6-2 μm. Moreover, the diaphragm is characterized by an area preferably in the range of 0.25-4 $mm^2$.

If the pores of the porous cover-plate material are selected to be small enough, the gas (mixture) passing through may be filtered in an extremely advantageous manner during the diffusion. Depending upon the pore size of the porous material, foreign matter such as soot and dirt particles or microbiological impurities may be removed from the gas (mixture) by this filtering.

The heating element and the temperature-dependent electrical resistors are preferably made of silver (Ag), gold (Au), nickel (Ni) or platinum (Pt). In one particularly advantageous refinement of the present invention, the cross-section of the heating element is of different size in the region of the contacting and in the heating zone. This may be advantageously used when sinter-fusing the cover plate onto the base plate.

The temperature-dependent electrical resistors and the heating element, respectively, may be protected from the influence of chemically aggressive gases and gas mixtures by a passivation layer. A silicon compound such as silicon oxide ($SiO_2$) and silicon nitride ($Si_3N_4$) primarily present themselves as substances for the passivation layer.

The thermal-conductivity sensor according to the present invention may be produced by adhering the porous cover plate onto the base plate. An adhesion of the base plate and cover plate presents itself in particular when the materials used have a different thermal expansion coefficient, since an adhesive connection is able to compensate for a different thermal expansion. This prevents thermally caused stresses in the joined materials. In particular, silver-filled adhesive agents having adapted coefficients of thermal expansion may be used as adhesive agents.

If there is only a slight difference in the thermal expansion coefficients between the porous cover plate made, for instance, of a porous ceramic material, and the base plate, it is also possible to directly encase the base plate with ceramic by sinter-fusing. For that purpose, prior to applying the material of the porous cover plate to be sintered, a resist layer, to be removed after the sintering process, for forming the cavity in the porous cover plate is applied on the base plate.

The heat necessary for the sintering process may be supplied from outside. However, the possibility also exists of effecting the sintering process solely by the resistance heat of the heating element. In this case, the diameter of the heating element, e.g., a platinum wire, may be substantially thicker in the heating zone than in the region of its contacting. In a particularly advantageous manner, the resist layer may also be removed by the resistance heat of the heating element, and thus a cavity having defined dimensions may be formed.

Moreover, the thermal-conductivity sensor of the present invention may be manufactured monolithically, avoiding the joining process between the base plate and cover plate. To this end, a layer of porous silicon is produced on the actual sensor base material of silicon; this is carried out in such a way that a cavity is formed between the subsequently formed diaphragm and the layer of porous silicon.

BRIEF DESCRIPTION OF THE DRAWINGS

In the following, several exemplary embodiments of the thermal-conductivity sensor according to the present invention, as well as methods for manufacturing it, are presented with reference to the figures.

DESCRIPTION OF EXAMPLE EMBODIMENTS

Figure 1:
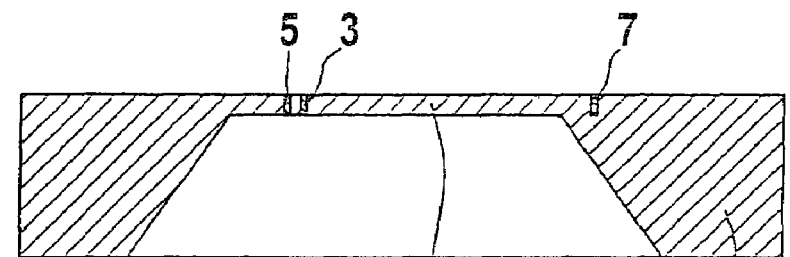
FIG. 1 shows the construction of a conventional micromechanical thermal-conductivity sensor in plan view (lower part) and in cross-section along the indicated line of intersection (upper part).

As the lower part of FIG. 1 shows, in a typical conventional micromechanical thermal-conductivity sensor, a heating element (resistance element) 3 in the form of a Pt-resistance wire and a temperature-dependent electrical resistor 5 for detecting diaphragm temperature $T_M$ are arranged in a meander form on silicon base plate 2 and diaphragm 1, respectively. Located outside of diaphragm 1 is a further temperature-dependent electrical resistor 7 for detecting ambient temperature $T_U$. Base plate 2, together with the applied electrical structures, forms a silicon sensor chip for measuring the thermal conductivity. In the upper part of FIG. 1, it can be seen that diaphragm 1 is formed as a recess in base plate 2.

To measure the thermal conductivity of the surrounding gas or gas mixture, for example, the heating power of the heating element needed to keep the difference between $T_M$ and $T_U$ constant is determined. Because of the small mass of the thin diaphragm and the materials applied thereon, very small thermal time constants may be achieved which are typically on the order of magnitude of milliseconds and below. Moreover, because of the thin diaphragm, the dissipation of heat via the surrounding gas is substantially greater than via the diaphragm material itself, resulting in great sensitivity of the sensor to changes in the thermal conductivity of the surrounding gas. The great sensitivity of the sensor also opens up the possibility of reducing the heat dissipation all in all, i.e., of lowering temperature difference $\Delta T$ between the diaphragm and the surroundings, which is reflected in a reduction of the electrical power loss of the sensor.

Figure 2:
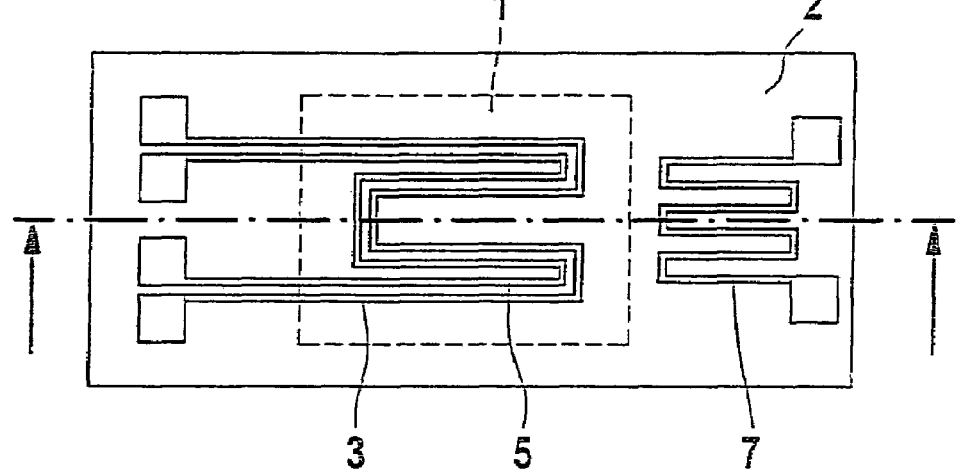
FIG. 2 shows a specific example embodiment of the thermal-conductivity sensor according to the present invention, in which a porous cover plate is stuck onto the silicon base plate on both sides of the diaphragm.
Figure 2:
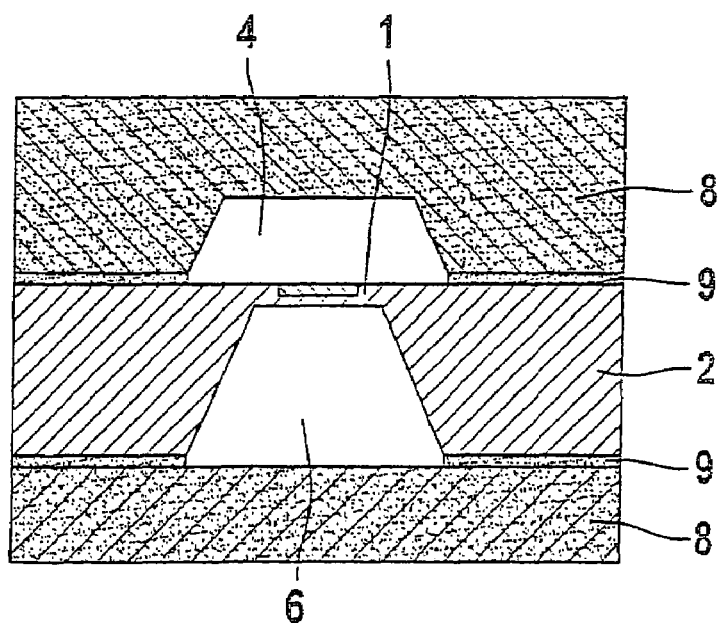
Figure 3A:
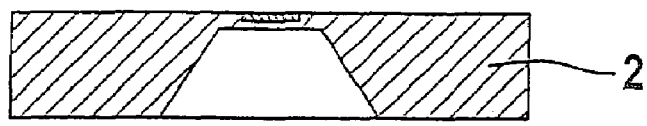
FIG. 3 shows another specific example embodiment of the thermal-conductivity sensor according to the present invention, in which a porous cover plate is sinter-fused onto the silicon base plate on both sides of the diaphragm.
Figure 3B:
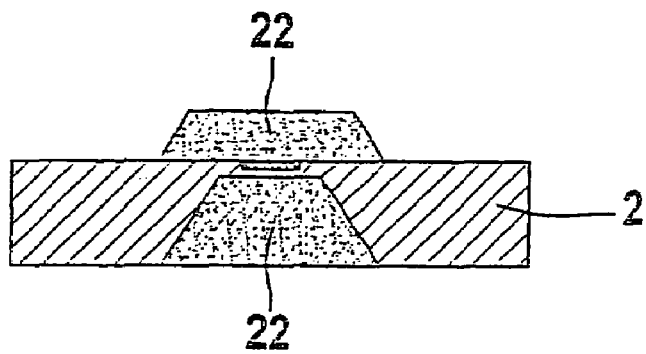
Figure 3C:
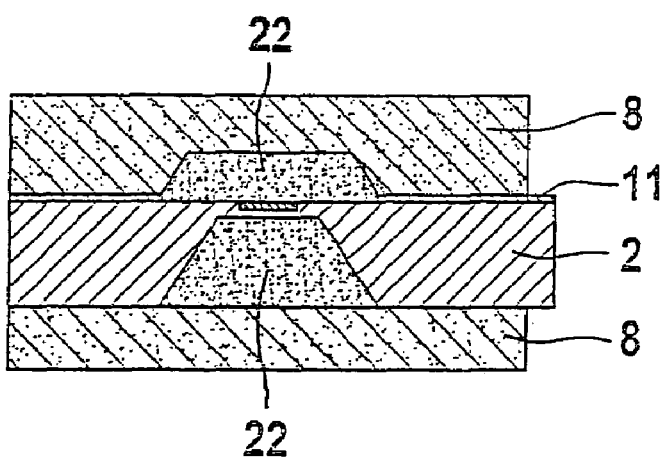
Figure 3D:
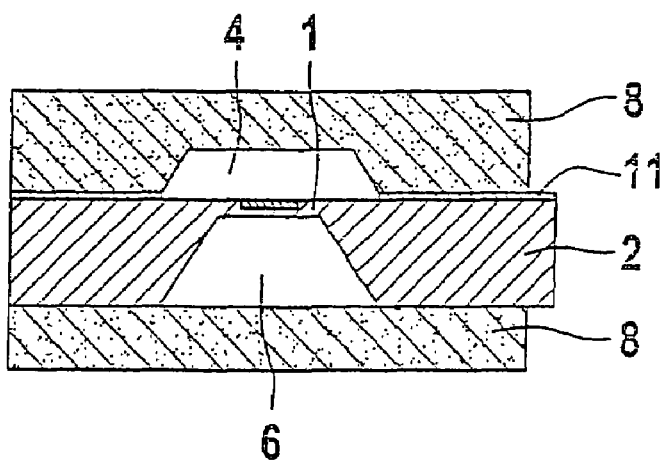

FIG. 2 shows a specific example embodiment of the thermal-conductivity sensor according to the present invention. A cover plate 8 made of porous ceramic is applied on both sides of the silicon sensor chip which is made up of base plate 2 together with applied current-conductive structures 3, 5. The recess of base plate 2, together with cover plate 8, forms a cavity 6 which is used as the measuring space for the sensor. On the other side of diaphragm 1, a recess is formed in cover plate 8; after cover plate 8 is applied on base plate 2, the recess forms a cavity 4 which is used as a further measuring space for the sensor. Both cover plates 8 are pasted onto the silicon sensor chip. Adhesive layers 9 are capable of compensating for any differences in the thermal expansion of ceramic cover plates 8 and the silicon sensor chip.

FIG. 3 shows another specific example embodiment of the thermal-conductivity sensor according to the present invention. In this case, a cover plate made of porous ceramic material is sinter-fused onto the silicon sensor chip on both sides of diaphragm 1. Because of the lack of possibility to compensate for different thermal expansions between the cover plates and the silicon sensor chip, cover plates 8 are only sinter-fused on if the thermal expansion coefficient of the ceramic material of the cover plates and the thermal expansion coefficient of the silicon sensor chip are very similar or identical. Before applying a paste or dispersion of the ceramic material for cover plates 8 on the silicon sensor chip, a resist layer 22 is applied in the region of heating element 3 and/or diaphragm 1, which is removed after the ceramic material is sintered. Cavities 4, 6 remain at the location of previous resist layer 22.

This production sequence is illustrated in FIG. 3. FIG. 3a) shows silicon sensor chip 2. FIG. 3b) shows silicon sensor chip 2 with applied resist layer 22. FIG. 3c) shows silicon sensor chip 2 with applied resist layer 22, as well as the ceramic material of cover plates 8 applied on both sides of the silicon sensor chip. Finally, FIG. 3d) shows cavities 4, 6 formed after the sintering process and removal of resist layer 22.

Both the sintering of the ceramic material of cover plates 8 and removal of resist layer 22 may be brought about by the resistance heat of Pt-resistance wire 3. For this purpose, the resist layer is made of a less heat-resistant, e.g., organic (sacrificial) material. A defined cavity may be created between the Pt-resistance wire and the porous ceramic encasing by way of the layer thickness of this material decomposing during the sintering process. To this end, Pt-resistance wire 3 has a different cross-section for the contacting and in the region of the heating zone. A bond 11 is applied on silicon sensor chip 2 for the electrical contacting.

FIG. 4 shows two further specific example embodiments of the thermal-conductivity sensor according to the present invention. In these specific embodiments, instead of a porous ceramic, porous silicon is used for cover plates 8. Because the thermal expansion coefficients of the cover plates and the silicon sensor chip are the same, thermally caused material stresses are avoided from the start.

Figure 4A:
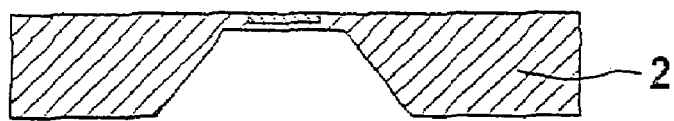
FIG. 4 shows two further specific example embodiments of the thermal-conductivity sensor according to the present invention, in which a porous cover plate of silicon is sinter-fused onto the silicon base plate on both sides of the diaphragm.
Figure 4B:
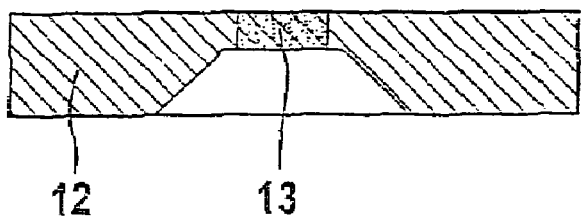

FIG. 4a) shows silicon sensor chip 2. FIG. 4b) shows a silicon wafer 12 having a porous region 13, silicon wafer 12 having a recess in porous region 13. Silicon wafer 12 is placed on silicon sensor chip 2 on both sides of diaphragm 1, in each case porous region 13 coming to rest over diaphragm 1.

Figure 4C:
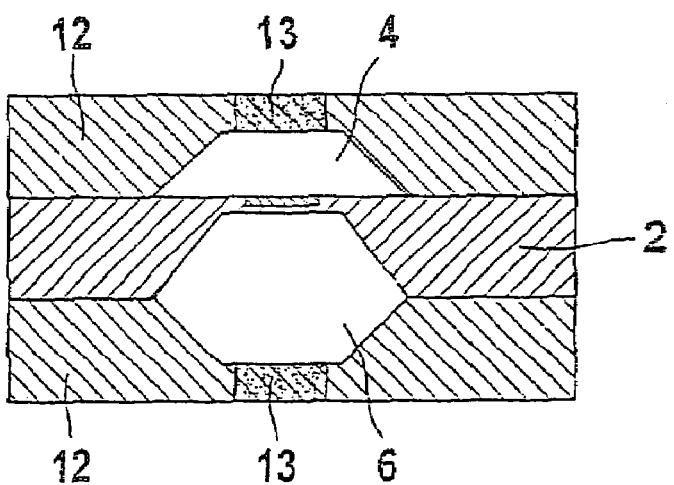

FIG. 4c) shows a variant, in which silicon wafer 12 is positioned in such a way on the side of diaphragm 1 on which the recess of silicon sensor chip 2 is located, that the cavities of silicon wafer 12 and of silicon sensor chip 2 form a common cavity having a larger volume.

Figure 4D:
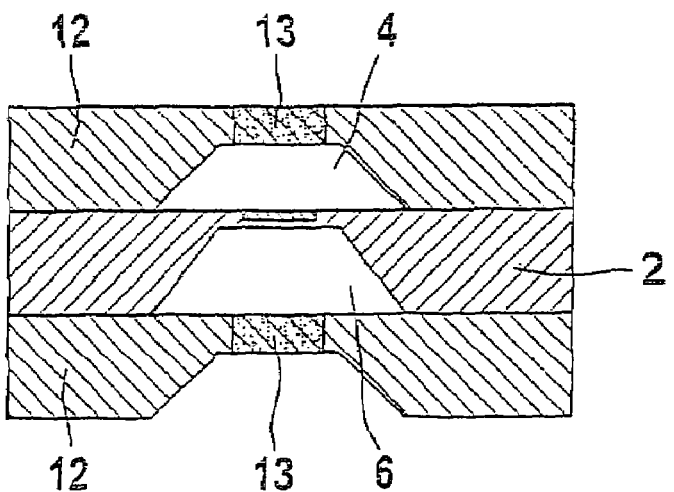

FIG. 4d) shows a further variant, in which silicon wafer 12 is positioned in such a way on the side of diaphragm 1 on which the recess of silicon sensor chip 2 is located, that the cavity of silicon sensor chip 2 remains unchanged. The arrangement of silicon wafer 12 on the respective opposite diaphragm side is the same for both variants of FIGS. 4c) and 4d).

In one particularly advantageous modification of the two variants indicated above, the costly joining process can be avoided, in that a layer of porous silicon is already produced on sensor chip 2, a cavity being formed between diaphragm 1 and the porous silicon layer. In this way, a monolithic thermal-conductivity sensor is obtained.

The micromechanical thermal-conductivity sensor according to the present invention is advantageously used for analyzing gases and gas mixtures which are analyzed in particular with respect to their type and concentration. In this context, binary gas mixtures are primarily suited for a quantitative analysis. Because of their comparatively high thermal conductivity, hydrogen gas ($H_2$) and helium (He) may be analyzed quickly and easily.

What is claimed is:

1. A micromechanical thermal-conductivity sensor, comprising:
   a thermally insulated diaphragm formed by a recess in a base plate exhibiting poor thermal conductivity;
   at least one heating element applied on the diaphragm;
   at least one temperature-dependent electrical resistor applied on the diaphragm for measuring a temperature of the diaphragm; and
   at least one further temperature-dependent electrical resistor applied outside the diaphragm on the base plate for measuring an ambient temperature;
   wherein the diaphragm is covered on at least one of its sides by a porous cover plate with a plurality of pores which permits gas exchange through diffusion, a cavity being left open between the diaphragm and the porous cover plate, the porous cover plate being secured on the base plate, and being made of at least one of a porous ceramic material or at least partially of porous silicon.

2. The micromechanical thermal-conductivity sensor as recited in claim 1, wherein the porous cover plate has a recess forming the cavity.

3. The micromechanical thermal-conductivity sensor as recited in claim 1, wherein the base plate is made of silicon.

4. The micromechanical thermal-conductivity sensor as recited in claim 1, wherein the porous cover plate is made of at least one of SiC and Al2O3.

5. The micromechanical thermal-conductivity sensor as recited in claim 4, wherein a thermal expansion coefficient of material of the porous cover plate is substantially the same as a thermal expansion coefficient of silicon.

6. The micromechanical thermal-conductivity sensor as recited in claim 1, wherein the diaphragm has an area in a range of 0.25-2 μm.

7. The micromechanical thermal-conductivity sensor as recited in claim 1, wherein the diaphragm has a thickness in a range of 0.6-2 μm.

8. The micromechanical thermal-conductivity sensor as recited in claim 1, wherein the cavity has a depth in a range of 0.1-2 μm.

9. The micromechanical thermal-conductivity sensor as recited in claim 1, wherein the porous cover plate filters a surrounding gas or gas mixture.

10. The micromechanical thermal-conductivity sensor as recited in claim 1, wherein the heating element and the temperature-dependent electrical resistor are made of one of silver (Ag), gold (Au), nickel (Ni) or platinum (Pt).

11. The micromechanical thermal-conductivity sensor as recited in claim 1, wherein the heating element has a different cross-section for contacting and in a region of a heating zone.

12. The micromechanical thermal-conductivity sensor as recited in claim 1, further comprising:
    a passivation layer, the at least one temperature-dependent electrical resistor and the at least one further temperature-dependent electrical resistor being protected against an influence of chemically aggressive gases or gas mixtures by the passivation layer.

13. The micromechanical thermal-conductivity sensor as recited in claim 12, wherein the passivation layer includes a silicon compound.

14. The micromechanical thermal-conductivity sensor as recited in claim 13, wherein the silicon compound is one of silicon oxide ($SiO_2$) or silicon nitride ($Si_3N_4$).

15. A method of using a micromechanical thermal-conductivity sensor, comprising:
    providing the micromechanical thermal conductivity sensor, the sensor including a thermally insulated diaphragm formed by a recess in a base plate exhibiting poor thermal conductivity;
    at least one heating element applied on the diaphragm;
    at least one temperature-dependent electrical resistor applied on the diaphragm for measuring a temperature of the diaphragm;
    at least one further temperature-dependent electrical resistor applied outside the diaphragm on the base plate for measuring an ambient temperature;
    wherein the diaphragm is being covered on at least one of its sides by a porous cover plate with a plurality of pores, the at least one porous cover plate which permits gas exchange through diffusion, a cavity being left open between the diaphragm and the porous cover plate, the porous cover plate being secured on the base plate, and the porous cover plate being made of at least one of a porous ceramic material or at least partially of porous silicon; and
    quantitatively analyzing one of a gas and a gas mixture using the sensor.

16. The method as recited in claim 15, wherein the gas mixture contains at least one of hydrogen (H2) and helium (He).

* * * * *